United States Patent

Artiushin et al.

[11] Patent Number: 5,712,090
[45] Date of Patent: Jan. 27, 1998

[54] PCR-BASED ASSAY FOR *MYCOPLASMA HYOPNEUMONIAE*

[75] Inventors: Sergey Artiushin, Ames, Iowa; László Stipkovits, Budapest, Hungary; F. Chris Minion, Ames, Iowa

[73] Assignee: Iowa State University Research Foundation, Inc., Ames, Iowa

[21] Appl. No.: 62,632

[22] Filed: May 18, 1993

[51] Int. Cl.⁶ .............................. C12Q 1/68; C12P 19/34; C07H 21/04

[52] U.S. Cl. .......................... 435/6; 435/91.2; 536/24.33; 536/24.32

[58] Field of Search .................. 435/6, 91.2; 536/24.33, 536/24.32

[56] References Cited

FOREIGN PATENT DOCUMENTS 54205  1/1991  Hungary.

*Primary Examiner*—Lisa B. Arthur
*Attorney, Agent, or Firm*—Dickstein, Shapiro, Morin & Oshinsky, LLP

[57] ABSTRACT

Disclosed herein is a PCR-based assay for *Mycoplasma hyopneumoniae*, a species-specific primer pair for use in the assay, and a related diagnostic kit. The primer pair is made up of an oligonucleotide having the nucleotide sequence 5'-AAGTTCATTCGCGCTAGCCC-3' and an oligonucleotide having the nucleotide sequence 5'-GCTCCTACTCCATATTGCCC-3'. Preferably, the kit contains an oligonucleotide probe having the sequence 5'-GGTAGCCCTTCCTTTGAGGT-3'.

14 Claims, 2 Drawing Sheets

FIG.1
FIG.2
FIG.3

```
   1  GGAATTCCAG CCAATCTTTT AATTAAAATT TTATCTTTAT ATTTGAAAAC TACCACATCA
  61  TTTCGCTGAG GTTTTTGAC ATTGTTAATA AAATTTGTT GGCCATTTTT TAAGGTTGGA
 121  AACATTGAGT TTCCTTCGAC ATTTATTAAT TGGTAGACAA AGATAAAAAG CGCAGAAACT
 181  ATTAAAACAC AAGTAAAAAT AAAAATAACA CCAATAATTA AGCGATTTTT CTTAATAAAT
 241  TTTAGAAATT TGTTACTTAA GTTTTTAGAT TTTAACATAG TTATTAAATC TATTTCTTTG
 301  ATATTTTATC ATAAAAAAAC AATTTTAATT TTTGATTTTA TAATAAAAAG TGCTGAATTT
 361  GAGGCAAACA TACTAATTAA TATAAAATTC TATAGTAAAA TAATTTGATT TAGTAAAGAA
 421  GTGACCTTTT ATTCTGATAT TTGCAAATAA TTCAATATTA TTCAATGTTT TATAAATATT
 481  CTTCTTTCCT TATTTTTACT TTTTTTTTTT TTTTTTTTT TTTGTTAAAA TTATTGCATA
 541  -GTAAAATTTA AGTTAAAACC CAACAAACCT AACTTATAAA ACCGAAAGGA ATTAGTAATA
 601  ATGCAAAATC TAAAAAAGAA TCTAAAAAAA ATATCCTTAT TTTTCGGAAT TTTTGGTTCT
 661  TTATGTACAA TTCTTACAAC AACCACAACA ACAATTTCTA TTAGAAATGA AAATGCAAAC
 721  GGGTTTTATT CGGGGACAGA AAATATTAAA AATGCAAGTT CAATAGCTTC TACAATTTTT
                                                      MHP3 →
 781  TCCTCTGCTC TGGACCCATT TAAATCGTTA AGTTCATTCG CGCTAGCCCA AAAATATGTA
 841  GATGATAAAT ATTTAAAAAT TGAACAAGAT AATTACGCAG GGAAATCTC GCTTCTCGGA
 901  GCAAAATCCA TAGTTTATTT TGGTGGATTA TTTTGGGAAG ATAAAGTTGC ATGAGCAAGT
 961  AATTTAACAG TAAAACATCA AAAAAAAGTA AGTCCATATT ATATAACAAG TAAGCCAAAA
1021  TATATTGAAG CAACCTTAAA AACTTGAACC TCGGGCTTAG GTAGCCCTTC CTTTGAGGTA
1081  GGCGGGGAAA TAAAATATAA TGGTAATTTC AGATCTAATT TAGGTATAAA AATTGGAATA
1141  GATTATGGAA CTAGAGAATT ATTTATTACT AAAAGTGTTC AAAACCTACC ACAAGCTAAA
                                                    ← MHP4
1201  ATAACTTATG CGGGTACGGG TTGGAGATAC AAAGTAACTT CATATGGCA ATATGGAGTA
1261  GGAGCAATAG AAACTGAAGA TGAATTTTTA ATGTTTAATA CTGAAAATTC AATGATTACA
1321  ACACGACGAA AAAGAAAACC TAAAACATCA TTTCCTGATA TTTTAGGTCG TTATATCGAA
1381  GAAAAATACG GCATTTACC TGAAGAAGAT GATAATAATT AATAACTTAA GTAAAAGTT
1441  TGAAACTAAA TCGATTTTTG AAAAAATTAA TTTAGAAATT CCCACAAACA AACTAACTTT
           MHP1 →
1501  TGTAGTTGGC GAATCTGGGA TGGGAAAATC AACCTTAATT AATTTAATTG CCGGTTTTAC
1561  TAAAAAAGAT GAAGGTGAAA TTATCTTTTT TAAAGATGGA AAAGAAGAAA AAAATCCTTT
1621  AATTGATGTA GTTTTTCAGG ATTTTAACCT AATTGAAAAT CTTTCTGTTA AAAATAATAT
1681  TTAATTGGA AATAGCTTAA TTCAAAAAGA ATTTGATCAA AATTTGCTTG AAAAAAGAGC
1741  AAATTTTCTT AATATTGAAA ATGAAAAACT AAATCAACAA GTCAAAGATT TATCGGGTGG
1801  CGAGAAACAA AGAGTCGGTA TTTTACGTGC TTTTTCGCGA AATTCAGATT TTATTTTACT
         ← MHP2
1861  CGATGAACCA ACCGGAAATC TTGATGAGGA AAATGCAGTT GCTGTTTTTG AAAATTTAAA
1921  AAATTATCA AAAAACAAAA CTATTTTGGT TGTTAGTCAC AATTTAGAAC TAGCAAAAAA
1981  ATATGCAGAT CAAATTATCC ATATCAAAAA AGATACTATT GATGTTGAAA CTTTTGACAA
2041  AAAGAAAAAA ACACAAGAAA ATGAGAGTGA AAATTCTGCT TTGTTTCAT AAATTGAACA
2101  AAAACCAGTT TTTAATTTTT TAACGAAATA TAAAACTGGT TTTTTGCTAG CTTTTGCCGA

2161  TTTTAAAACA AAAATAACAA CTTTTATTTT ATTAATTATT GTTTTTTTTG TTTTTATAAG
2221  TGGGGGCACA TTGTTCACTT CACTACAGAT TTCTGCAAAA AATCTCAATT TGTCTAAGGT
2281  CCAGGAATAT AGTATGGACT CAGTAATTAT AAATAGACCA TTTATAGGAA TTCC
```

FIGURE 4

PCR-BASED ASSAY FOR *MYCOPLASMA HYOPNEUMONIAE*

US GOVERNMENT RIGHTS

The United States Government has certain rights in the invention described and claimed herein as a result of its support of certain work related to the invention under grants from the United States Department of Agriculture USDA Grant 91-37204-6488 and the National Institute of Allergy and Infectious Diseases NIH Grant #K04AI01021.

FIELD OF THE INVENTION

This invention relates to diagnostic assays for the detection of microorganisms in a specimen and more particularly to a PCR-based assay for *Mycoplasma hyopneumoniae*, primers specific for the DNA of *M. hyopneumoniae*, and diagnostic kits for detecting *M. hyopneumoniae* in a specimen.

REFERENCES

Several publications are referenced herein by Arabic numerals within parenthesis. Full citations for these references may be found at the end of the specification immediately preceding the claims. The disclosures of these publications and any other publication referenced herein are hereby incorporated herein by reference in their entirety unless otherwise noted.

BACKGROUND OF THE INVENTION

*Mycoplasma hyopneumoniae* (Mhp) is the etiological agent of swine mycoplasma pneumonia, a chronic disease of high economical impact. The disease is characterized by low mortality but high morbidity, and its economic impact is due to growth retardation and a feeding efficiency reduction in infected swine (1). Despite a variety of approaches and repeated attempts, vaccines have not proven effective in preventing colonization or reducing disease in swine populations. Maintenance of cesarean-derived mycoplasma-free swine herds is marginally effective because of the difficulty in maintaining total isolation in swine (2). Eradication of this pathogen in chronically-infected animals through detection and elimination has not been possible because of difficulties in detection and maintenance of disease-free herds. The isolation of Mhp requires specialized media and extended incubation, and reproducible isolation from clinical samples requires strict adherence to media quality control. Serological analysis is often used, but serological cross-reactions with *M. hyorhinis* or the nonpathogenic *M. flocculare* complicates analysis (3, 4) and is not generally accepted as a reliable diagnostic method.

Alternative methods for detection of Mhp based on DNA-DNA or DNA-RNA hybridization have been developed (5, 6). These systems used either cloned fragments of DNA or synthetic oligonucleotides that exhibited species-specific reactivity. All of these probes suffer from low sensitivity and consequently have not gained wide acceptance in the diagnostic field. Attempts to identify Mhp in nasal and lung washings from infected pigs have failed because of low sensitivity with non-radioactively labeled probes. Increased sensitivity can be obtained using 16S/23S rRNA-specific probes (6) because of the higher copy number of ribosomal sequences relative to a single copy chromosomal sequence.

The polymerase chain reaction (PCR) has demonstrated enhanced sensitivity over ribosomal RNA probes (7). PCR detection has been applied to a number of important bacterial pathogens, including mycoplasmas (8, 9).

None of these alternative methods have been shown to identify field isolates of Mhp. We have developed a sensitive and specific PCR-based assay for field isolates of Mhp, based upon a species-specific primer pair. This permits faster and better identification of Mhp in swine, which will permit faster treatment and better control of the disease.

SUMMARY OF THE INVENTION

It is an object of the invention to provide PCR primers for use in a PCR-based assay for *M. hyopneumoniae*.

Another object of the invention is to provide a diagnostic kit for use in detecting or measuring the presence of *M. hyopneumoniae* DNA in a sample.

A further object of the invention is to provide a method for detecting or measuring the presence of *M. hyopneumoniae* in a sample.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

To achieve the objects and in accordance with the purpose of the invention, as embodied and broadly described herein, the present invention provides a species-specific polymerase chain reaction (PCR)-based diagnostic assay and reagents for the identification of *Mycoplasma hyopneumoniae* (Mhp). The assay is based upon a primer pair for a target nucleic acid sequence in Mhp DNA that is believed to be species-specific. In the method of the invention, the presence of Mhp in a sample is detected or measured by the steps of: (1) isolating the DNA from the Mhp in the sample; (2) amplifying the quantity of the target nucleic acid sequence in the isolated DNA by PCR, using the primer pair of the invention; and (3) detecting or measuring the presence of the amplified target nucleic acid sequence.

The invention further includes a kit for use in detecting or measuring the presence of Mhp DNA in a sample suspected of containing such DNA. The kit comprises a container and the primer pair of the invention in such container. Preferably, the kit further comprises a probe that hybridizes to the target nucleic acid sequence amplified by the use of the primer pair in the polymerase chain reaction.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1 shows a comparison of Mhp and *M. flocculare* reactivity to PCR primer pairs MHP1/2 and MHP3/4. DNA of Mhp (1 ng) and *M. flocculare* (100 ng) were subjected to PCR amplification as described in the Materials and Methods. One tenth of the reaction mixtures were examined by ethidium bromide —agarose gel electrophoresis (2% agarose). Lanes 1–6 contain reactions with the PCR primer pair MHP1/2 and lanes 8–14 with the PCR primer pair MHP3/4. The following DNAs were amplified: lanes 1 and 9, Mhp J; lanes 2 and 10, Mhp 232; lanes 3 and 11, *M. flocculare* 10019; lanes 4 and 12, *M. flocculare* 10020; lanes 5 and 13, *M. flocculare* 18057; lanes 6 and 14, *M. flocculare* 2739; lane 7, kb ladder size standard; lane 8, PCR reaction with no DNA added.

FIG. 2 shows the results of PCR amplification of Mhp field isolate DNAs with the MHP3/4 PCR primer pair. PCR products from reactions with the same DNAs with annealing temperatures of 58° C. (upper panel) and 56° C. (lower panel) are shown.

FIG. 3 shows a determination of PCR sensitivity of amplification of Mhp strain J DNA with the MHP3/4 primer pair. Each reaction was performed as described in Example 1 with 30 cycles of amplification. The amount of DNA added to each reaction mixture shown in lanes 1–6 is 10 ng, 1 ng, 0.1 ng, 0.01 ng, 0.001 ng, and 0.0001 ng respectively. Lane 7 contained no DNA and lane 8, kb ladder size standards.

FIG. 4 shows the DNA sequence of a 2.3 kb fragment of M. hyopneumoniae chromosomal DNA.

DETAILED DESCRIPTION OF THE INVENTION

Reference will now be made in detail to the presently preferred embodiments of the invention, which, together with the following example, serve to explain the principles of the invention.

The invention relates to a PCR-based assay that is specific for M. hyopneumoniae (Mhp). It is based upon a pair of species-specific primers that are used in the assay. The primers, in turn, are based upon a target nucleic acid sequence that is specific for Mhp. As used herein, the term "target nucleic acid sequence" is a portion or segment of Mhp chromosomal DNA represented by a specific sequence of specific nucleotides. The quantity of this part of the DNA will be amplified by the polymerase chain reaction.

The primer pair comprises an oligonucleotide having the nucleotide sequence 5'-AAGTTCATTCGCGCTAGCCC-3' (SEQ ID NO: 1) and an oligonucleotide having the nucleotide sequence 5'-GCTCCTACTCCATATTGCCC-3' (SEQ ID NO: 2). The primers have a higher GC than AT content, having a GC content of approximately 55%. This permits them to be used at a higher annealing temperature. This limits the problem of false priming and provides for a more specific reaction.

The primers are used in a PCR-based assay for detecting the presence of Mhp in a sample. The DNA from the Mhp in the sample is isolated by standard techniques. The quantity of the target nucleic acid sequence in the isolated DNA that is species-specific for Mhp is then amplified by PCR, using the primer pair of the invention. The presence of the amplified quantity of the target nucleic acid sequence in this second sample is then detected by standard techniques.

The target nucleic acid sequence was determined by analysis of the 2.3 kb Mhp chromosomal DNA fragment identified in Example 1, the sequence SEQ ID NO:4 of which is shown in FIG. 4. Standard computer algorithms, based upon the estimated melting temperature, potential secondary structure, and other factors known to those skilled in the art, were applied to the sequence shown in FIG. 4 to identify primer candidates, from which the primers of the invention were selected. (See Rychilk and Rhoads, "A Computer Program for Choosing Optimal Oligonucleotides for Filter Hybridization, Sequencing, and In Vitro Amplification of DNA," Nucleic Acids Research, 17:8543–8551 (1989), incorporated herein by reference.) The MHP 3/4 primer pair binds to the sequence as shown in the figure, thereby identifying a target nucleic acid sequence comprising nucleotides 810 to 1264 of the sequence shown in FIG. 4.

The DNA is isolated from the microorganism by standard techniques. Basically, the cell walls are disrupted, and the DNA is extracted. Preferably, the DNA is precipitated and resuspended in buffer.

The target nucleic acid sequence in the extracted DNA is amplified by the use of the polymerase chain reaction in conjunction with the teachings contained herein. The PCR technique is well known. See U.S. Pat. No. 4,683,195, issued Jul. 28, 1987 to Mullis et al., U.S. Pat. No. 4,683,202, issued Jul. 28, 1987 to Mullis, U.S. Pat. No. 4,800,159 issued Jan. 24, 1989 to Mullis et al., U.S. Pat. No. 4,965,188, issued Oct. 23, 1990 to Mullis et al., U.S. Pat. No. 4,889,818, issued Dec. 26, 1989, to Gelfand et al., and U.S. Pat. No. 4,902,624, issued Feb. 20, 1990, to Columbus et al., all of which are incorporated herein by reference. See also Bej et al., "Amplification of Nucleic Acids by Polymerase Chain Reaction (PCR) and Other Methods and Their Applications," Critical Reviews in Biochemistry and Molecular Biology, 26(3/4):301–334(1991), which is also incorporated herein by reference.

In general, the polymerase chain reaction involves the use of a pair of specific oligonucleotide primers to initiate DNA synthesis on a target DNA template. Two oligonucleotide primers are used for each double-stranded sequence to be amplified. The target sequence is denatured into its complimentary strands. Each of the primers, which are sufficiently complementary to a portion of each strand of the target sequence to hybridize with it, anneals to one of the strands. The primers are extended, using nucleosides in the sample and a polymerization agent, such as heat-stable Taq DNA polymerase. This results in the formation of complementary primer extension products, which are hybridized to the complementary strands of the target sequence. The primer extension products are then separated from the template strands, and the process is repeated until the desired level of amplification is obtained. In subsequent cycles, the primer extension products serve as new templates for synthesizing the desired nucleic acid sequence.

More specifically, the sample containing the isolated Mhp DNA is heated in the presence of the four different nucleoside triphosphates and the primer pair for an effective time and at an effective temperature to denature the DNA in the sample. Each oligonucleotide primer is sufficiently complementary to different strands of the target nucleic acid sequence to hyridize with them, such that an extension product is synthesized from each oligonucleotide primer. When separated from its complement, the extension product serves as a template for the synthesis of the extension product of the other oligonucleotide primer. Preferably, the temperature is in the range 85° C. to 95° C. and most preferably is at about 92° C. The time is from 0.5 minute–4 minutes and preferably about two minutes. Preferably, the nucleoside triphosphates are deoxyribonucleoside triphosphates.

The denatured DNA is then cooled to a temperature that promotes hybridization, i.e., annealing, of each oligonucleotide primer to its complementary strand. Preferably, this temperature is from 54° C. to 58° C. and most preferably about 56° C.

The natured DNA is contacted with a thermostable enzyme that catalyzes the combination of the nucleoside triphosphates to form primer extension products complementary to each strand of DNA. The thermostable enzyme is preferably a polymerase from Thermus aquaticus. Most preferably the polymerase is Taq polymerase. The thermostable enzyme can be added after the denaturing or annealing steps or at the same time.

This mixture is maintained at an effective temperature and for an effective time to promote the activity of the enzyme and to synthesize, for the target nucleic acid sequence being detected, an extension product of each oligonucleotide primer that is complementary to each strand of the sequence. The temperature must not be so high as to separate each extension product from its complementary strand at this point. The temperature can range from 55°–85° C. and most preferably is about 72° C. The time is 0.5–4 minutes, preferably about 1 minute.

These steps are then repeated with the primer extension products. The annealed DNA is denatured by heating the mixture from the previous step for an effective time and at an effective temperature to separate the primer extension products from the strands on which they were synthesized to produce single stranded molecules. However, the temperature must not be so high as to denature the enzyme irreversibly. Preferably, the temperature is from 85° C. to 95° C. and most preferably about 92° C. The time is from 0.5 minute to 4 minutes and most preferably about 1 minute.

This mixture is then cooled for an effective time and to an effective temperature to promote hybridization (annealing) of each oligonucleotide primer to its complementary single-stranded molecule produced by the prior step, and the mixture is maintained at an effective temperature and for an effective time to promote the activity of the enzyme and to synthesize an extension product of each oligonucleotide primer that is complementary to each strand of the target nucleic acid sequence being detected. Preferably, the temperature is from 85° C. to 95° C. and preferably about 92° C. Preferably, the time is from 0.5 minute to 4 minutes and most preferably about 1 minute. This results in the amplification in the quantity of the target nucleic acid sequence, if it is present. This step of primer extension and the prior step of annealing may be carried out simultaneously or sequencially.

The cycle of denaturing, annealing, and primer extension is carried out at least 20 times, preferably 30 times.

The amplified DNA is detected by standard techniques in conjunction with the teachings contained herein. For example, it can be detected by a probe or by the use of gel electrophoresis.

When a probe is used, the amplified DNA is rendered single stranded. The probe is brought into contact with a mixture containing the denatured amplified target nucleic acid sequence. A determination is made whether or not hybridization has occurred. Preferably, the probe is an oligonucleotide that has been labeled with a detectible entity.

The probes can be prepared by standard techniques known to those skilled in the art, given the target sequence of the invention and the teachings contained herein. Preferably, the probe is an oligonucleotide with about 17 to about 27 nucleotides that hybridizes to the target sequence. More preferably, it is about 21 to 27 nucleotides in length. Preferably, the GC is content is at least 50% and most preferably 55%. The preferred probe of the invention is 5'-GGTAGCCCTTCCTTTGAGGT-3' (SEQ ID NO: 3).

A detectable entity is attached to the oligonucleotide. Such detectable entity is a detectable molecule or compound, such as a radioactive isotype or biotin.

Alternatively, the PCR product can be detected by electrophoresing it on a gel, which separates the DNA by molecular weight. The amplified DNA will appear as a single band at a certain size with reference to molecular weight standards. The band is visualized by standard techniques, such as staining with ethidium bromide followed by illumination with ultraviolet light.

The invention also includes a kit for use in detecting the presence of Mhp DNA in a sample suspected of containing it by detecting the target nucleic acid sequence within the DNA. The kit comprises a container and the primer pair of the invention within the container. Preferably, it also contains a probe that hybridizes to the target nucleic acid sequence amplified by the use of the primer pair of the invention in the polymerase chain reaction. Most preferably, the kit further contains a nucleic acid polymerase, preferably Taq, and additional means, such as reagents, for detecting the hybridization of the probe to the amplified DNA.

It is to be understood that the application of the teachings of the present invention to a specific problem or environment will be within the capabilities with one having ordinary skill in the art in light of the teachings contained herein. Examples of the products and processes of the present invention appear in the following example.

EXAMPLE 1

Development of Polymerase Chain Reaction Primers to Detect *Mycoplasma hyopneumoniae*

The purpose of this study was to develop a species-specific polymerase chain reaction (PCR)-based diagnostic reagent for the identification of Mhp. Based upon DNA sequence analysis of a cloned fragment of Mhp DNA, two pairs of PCR primers were constructed and tested against different strains of Mhp, *Mycoplasma flocculare*, other mycoplasma species, and non-Mollicute microorganisms which commonly inhabit the respiratory tracts of swine. A total of 40 field isolates of Mhp and 6 field isolates of *M. flocculare* have been examined. One pair of primers, MHP1/2, gave a nonspecific reaction with *M. flocculare*, *Mycoplasma hyorhinis*, and *Mycoplasma hyosynoviae*. The second primer pair, MHP3/4, gave a positive signal in PCR with Mhp reference strains and all 40 Mhp field isolates, but not with other Mollicutes or microorganisms. Examination of the protein patterns of the non-reactive strains by SDS-PAGE indicated a significant protein variation in these isolates as compared to the reference strains and PCR positive isolates. These results indicate that Mhp is genetically heterologous and displays significant protein variability.

MATERIALS AND METHODS

Organisms and culture conditions

The mycoplasma and other bacterial strains used in this study as the source of chromosomal DNA for positive and negative samples in the PCR reactions are listed in Table 1. All mycoplasmas were grown and maintained in Friis medium supplemented with 20% horse serum and fresh yeast extract (10). Field isolates of Mhp representing 40 isolates from different sources were obtained from Dr. R. F. Ross at the Veterinary Medical Research Institute, Iowa State University. All strains were stocked at −70 C. All field isolates were typed using fluorescence antibody (11) and/or metabolic inhibition (12), and in some instances, protein profiles were compared using sodium dodecyl sulfate polyacrylamide gel electrophoresis (13).

Construction and screening of the Mhp genomic DNA library

A Mhp gene library in pUC19 was prepared as follows. DNA was prepared according to known methods (14). The purity and concentration was determined spectrophotometrically. The ratios of optical densities at 260 and 280 were more than 1.8–2.0. Plasmid DNA was obtained as previously described (15). DNA of *M. hyopneumoniae* strain J was digested by EcoR1. Fragments of 1–4 kb were separated on agarose gel and ligated into EcoR1 sites of plasmid pUC19, which was used for transformation of *E. coli* JM109 (16). Clones of recombinants of white color were checked by in situ hybridization with DNAs of *M. hyopneumoniae* and *M. flocculure*. The selected clones were used for DNA preparation, and they were analyzed by dot-blot and Southern blot hybridization (17). DNAs of mycoplasmas and plasmids were labeled by $^{32}$P by nick translation (18). The hybridization was performed for 12 hours at 60° C. in a mixture of 2×SSC, 0.2% SDS, 5×Denhardt solution, and 100 mg/ml DNA of salmon sperm. Filters were washed after hybridization with 2×SSC containing 0.2% SDS at room temperature and with 0.2×SSC containing 0.2% SDS at 60° C. The insert of the final specific plasmid recombinant was analyzed by EcoR1, NdeI, and DraI.

Two hundred and eighty-two clones of recombinant plasmids were examined. At first, 28 clones giving strong hybridization only with DNA of *M. hyopneumoniae* were selected. Dot-blot hybridization of the recombinant plasmids of the selected clones with $^{32}$P labeled DNAs of *M. hyopneumoniae, M. hyorhinis, M. hyosynoviae, A. granularum*, and *A. laidlawii* was done. Based on a comparison of the hybridizations, we selected for further study plasmids A8, B3, C4, C9, and D7, which were renamed pMhp01, pMhp02, pMhp03, pMhp04, pMhp05, and pMhp06. They contained inserts of *M. hyopneumoniae* of 1–4.5 kb. Southern-blot hybridization of these plasmids with DNAs of *M. hyopneumoniae, M. flocculure, M. hyorhinis*, and *M. hyosynoviae* labeled with $^{32}$P was done. Filters exposed 15 hours after hybridization showed positive reaction of all inserts with only DNA of *M. hyopneumoniae*. After a 72 hour exposure of the filters, a slight hybridization signal was observed between DNA of *M. flocculare* and plasmids pMhp01, pMhp02, pMhp03, and pMhp06 and between DNA of *M. hyorhinis* and pMhp03 and pMhp04 as well as between *M. hyosynoviae* and plasmid pMhp01. Based on these results, pMhp05 was selected as potential source for a gene probe for the identification of *M. hyopneumoniae*. This plasmid harbored a 2.3 kb insert of Mhp chromosomal DNA.

Further hybridization testing with pMhp05 failed to demonstrate reactivity to *M. gallisepticum, M. arginini, M. synoviae, M. flocculare*, and *A. axanthum* chromosomal DNAs. Also there was no reaction to the DNA obtained from the spleen and lung of gnotobiotic piglets or to DNAs from other bacterial swine pathogens including *Escherichia coli, Salmonella gallinarum, Staphylococcus aureus, Bordetella bronchiseptica, Erysipelothrix rhusiophiae, Haemophilus parasuis, Corynebacterium pyogenes*, and *Pasteurella multocida*.

DNA sequencing and PCR primer selection

The DNA sequence of the 2.3 kb fragment of Mhp chromosomal DNA in plasmid Mhp05 was obtained using standard dideoxy sequencing techniques (19). A series of deletion mutants was constructed by the method of Henikoff (20) described by Maniatis et al. (15) to aid in the sequencing. Alignment of overlapping sequences was performed using the DNASIS software program (Hitachi Software Engineering America, Ltd. San Diego, Calif.). Four 20 base pair nucleotide sequences were chosen as potential PCR primers using the DNASIS and OLIGO (Northern Biosciences, Minneapolis, Minn.) software programs. The primer sequences used in this study were as follows: MHP1 (5'-TGTGTAGTTGGCCAATCTGG-3') SEQ ID NO:5; MHP2 (5'-GATTTCCGGTTGGTTCATCG-3') SEQ ID NO:6; MHP3 (5'-AAGTTCATTCGCGCTAGCCC-3') SEQ ID NO:1; and MHP4 (5'-GCTCCTACTCCATATTGCCC-3') SEQ ID NO:2.

Preparation of samples for PCR

DNA from mycoplasma cultures was isolated by a modification of the method of Marmur as described by Maniatis et al. (15). Briefly, 100 µl of 30 mM Tris-HCl—30 mM EDTA—300 µg/ml Proteinase K (pH 8.0) was added to 200 µl of an overnight culture. The preparation was incubated at 50° C. for one hour and extracted once with phenol/chloroform (1:1) and once with chloroform. The DNA was coprecipitated with yeast tRNA by adding two volumes of ethanol, and the pellet was dissolved in 20 µl of TE buffer (10 mM Tris-HCl—0.05 mM EDTA, pH 8.0). DNA concentrations were determined by fluorescence using the Bio-Rad model TKO 100 Mini-Fluorimeter (Bio-Rad Laboratories, Richmond, Calif.).

DNA amplification by PCR

Oligonucleotides were synthesized by standard methods using an automated DNA synthesizer (Applied Biosystems DNA synthesizer, Foster City, Calif.). PCR reactions were performed in a final volume of 50 µl containing 50 mM KCl, 10 mM Tris-HCl (pH 9.0), 01% Triton X-100, 4 mM MgCl, 0.11 µM primers, 40 µM of each deoxynucleoside triphosphates, and 0.5 unit of Taq DNA Polymerase (Gibco BRL, Gaithersburg, Md.). An overlay of mineral oil was added to each tube followed by denaturation at 92° C. for 2 min. Cycling parameters that gave the best results were 92° C. for 1 min., 56° C. for 1 min., 72° C. for 1 min for 30 cycles. The final cycle included a 3 minute primer extension step at 72° C. to completely extend all amplification products. Following amplification, mineral oil was removed from aqueous PCR reagent mixtures, 5 to 10 µl of the reaction mixture was electrophoresed in a 2% agarose gel, and the PCR products were visualized by ethidium bromide staining and UV illumination.

RESULTS

A genomic library of Mhp chromosomal DNA was constructed in plasmid pUC19 and screened for species-specific fragments. One 2.3 kb fragment was selected for further study based upon its lack of hybridization with other swine commensal and pathogenic bacteria. A total of 6 Mhp field isolates were tested in DNA-DNA hybridization reactions in this earlier study, and all reacted positively.

Two primer pairs were selected using the OLIGO and DNASIS software programs. The two primer pairs, MHP1/2 and MHP3/4, had a 50% and 55% GC mol % content, respectively. The specificity of the primer pairs was evaluated using chromosomal DNA from different mycoplasma species and strains in PCR reactions. The MHP1/2 primer pair gave a positive signal not only with the DNA from Mhp, but also with the DNA of *M. flocculare* (FIG. 1), *M. hyorhinis* and *M. hyosynoviae* (data not shown). With DNA from Mhp and *M. flocculare*, a 390 bp band was observed with the MHP1/2 primer pair (FIG. 1). The second primer pair (MHP3/4) gave positive results with DNA from Mhp, but not with DNA from *M. flocculare* (FIG. 1). Primer pair MHP3/4 failed to produce a reaction product using DNA from other mycoplasmas, bacteria or swine tissues (data not shown).

A total of 40 field strains were examined by PCR using the MHP3/4 primer pair. See Table 1. Each of these isolates reacted positively with the MHP3/4 primer, but in preliminary studies when annealing temperatures were at 58° C., a weak band was observed in 22 of the 40 field isolates (FIG. 2). This was in contrast to the type strains 232A and J, which consistently gave a strong band with the MHP3/4 primer pair. To determine the optimum reaction conditions for all Mhp strains, PCR reactions were performed at different annealing temperatures (54°–58° C.) and different magnesium concentrations (0–10 mM) with the Mhp J strain as well as several variant field isolates. With the MHP1/2 primer pair, the optimal magnesium concentration was 2 mM, and with the MHP3/4 primer pair, the optimal concentration was 4 mM. There was no difference in the PCR reaction using the MHP 3/4 primer pair with the J strain when the annealing temperature was varied from 54°–58° C. (data not shown). The variant field isolates, however, gave a much stronger band when the annealing temperature was lowered 2° C. to 56° C. (FIG. 2). The protein patterns of field isolates that reacted strongly with the MHP 3/4 primer pair at 58° C. was compared to several that reacted weakly by SDS-PAGE. From a limited analysis, the field strains could be divided into two distinct patterns (data not shown). At all annealing temperatures used, DNAs from other mycoplasma species failed to react (data not shown). Variability in the quantity of amplified fragments was observed with DNA from some field isolates (FIG. 2). This was assumed to be due to either the quantity or quality of the template DNA. However, differences in the amplified sequences of some of the field isolates could not be ruled out.

The sensitivity of the MHP3/4 PCR primer pair was determined by varying the quantity of template DNA in the PCR reaction as shown in FIG. 3. Positive products could be observed at DNA concentrations as low as 1 picogram of DNA.

DISCUSSION AND CONCLUSIONS

Enzootic pneumonia is one of the more important diseases in swine populations, resulting in significant economic losses worldwide. Since there are no effective vaccines against the causative organism, Mhp, control of the disease depends upon accurate diagnosis and elimination of infected swine. Diagnosis of Mhp infection is presently based on isolation and characterization of cultures from clinical samples, and the attendant pathomorphological and serological investigations. All of these methods are difficult, insensitive, time consuming and are often not sufficiently reliable. To overcome these problems, significant effort has been made in the development of new diagnostic reagents and tests. Included are more rapid and sensitive enzyme-linked immunosorbent assays (21), DNA-DNA hybridization probes (6), and PCR (8).

The most promising technology is PCR, which has been shown capable of detecting as few as 4 organisms in clinical samples (22). It is also an exquisitely specific technique, but problems can still arise because of genomic diversity in environmental samples. Our results support this idea, since the 40 Mhp field isolates could be separated into two distinct groups based upon their PCR patterns at two different annealing temperatures. The DNA sequence variability responsible for this diversity is not known.

The MHP 3/4 primer pair described in this example produces a 474 base pair fragment with all Mhp isolates tested, but failed to react with other mycoplasma or bacterial DNAs. The sensitivity demonstrated with primer pair MHP3/4 was approximately 1 pg after 30 cycles of amplification (FIG. 3). Based on previous studies of detection of mycoplasmas in clinical samples (22), this level of sensitivity should be adequate for the identification of Mhp in swine respiratory tissues and possibly in tracheal swabs. Increased sensitivity could be achieved either by increasing the number of PCR cycles, the use of radioactivity, a second round of amplification with a pair of inner primers, or other signal enhancing techniques (7, 23). For example, in one experiment, 5 additional cycles of amplification resulted in a 10-fold increase in sensitivity (data not shown).

TABLE 1

| STRAINS AND PCR RESULTS | | | |
|---|---|---|---|
| Strain | Source | MHP1/2 | MHP3/4 |
| *M. Hyopneumoniae* | | | |
| 1361A | IVDL+ | ++ | ++ |
| 1375C | IVDL | ++ | ++ |
| 1417 | IVDL | ++ | ++ |
| 1419 | IVDL | ++ | + |
| 1424B | IVDL | ++ | ++ |
| 1472C | IVDL | ++ | + |
| 1363 | IVDL | ++ | + |
| 1375A | IVDL | ++ | ++ |
| 1378A | IVDL | ++ | ++ |
| 1381A | IVDL | ++ | ++ |
| 1416B | IVDL | ++ | + |
| 1464A | IVDL | ++ | + |
| 8489 | IVDL + Chen | ++ | + |
| 8765 | IVDL + Chen | ++ | ++ |
| 9078 | IVDL + Chen | ++ | + |
| 9275 | IVDL + Chen | ++ | + |
| 10731 | IVDL + Chen | ++ | + |
| 10986 | IVDL + Chen | ++ | + |
| 11684C | IVDL + Chen | ++ | + |
| 8689 | IVDL + Chen | ++ | ++ |
| 10954 | IVDL + Chen | ++ | + |
| 11928 | IVDL + Chen | ++ | + |
| P + 1814S | Armstrong | ++ | ++ |
| P + 1814 + 10 | Armstrong | ++ | + |
| P + 5398 + 1 | Armstrong | ++ | + |
| P + 5782 | Armstrong | ++ | + |
| P + 6053 + 2 | Armstrong | ++ | ++ |
| P + 6053 + 3 | Armstrong | ++ | + |
| P + 6053 + 4 | Armstrong | ++ | + |
| P + 11318 + 6 | Armstrong | ++ | + |
| P + 12895 + 2 | Armstrong | ++ | + |
| P + 13129 + 6 | Armstrong | ++ | ++ |
| P + 13129 + 9 | Armstrong | ++ | ++ |
| 31 + 9 | PIC + BZE | ++ | ++ |
| 37 + 9 | PIC + BZE | ++ | ++ |
| 3 + 14 | PIC + BZE | ++ | ++ |
| 4 + 14 | PIC + BZE | ++ | ++ |
| 16 + 14 | PIC + BZE | ++ | ++ |
| 18 + 14 | PIC + BZE | ++ | ++ |
| 232A | Ross | ++ | ++ |
| J | Ross | ++ | ++ |
| *M. flocculare* | | | |
| 10019 | Stipkovits | ++ | − |
| 10020 | Stipkovits | ++ | − |
| 18057 | Stipkovits | ++ | − |
| 2739 | Stipkovits | ++ | − |
| MS42 | Stipkovits | ++ | − |
| *M. gallisepticum* | Minion | − | − |
| *M. hyosynoviae* | Stipkovits | ++ | − |
| 25591 | ATCC | ++ | − |
| *M. hyorhinis* | Stipkovits | ++ | − |
| GDL | Ross | ++ | − |
| *M. pulmonis* | Minion | − | − |
| *A. laidlawii* | Minion | − | − |
| *A. granularum* | Stipkovits | − | − |
| *A. axanthum* | Stipkovits | − | − |
| *Escherichia coli* | Stipkovits | − | − |
| *Salmonella gallinarum* | Stipkovits | − | − |
| *Staphylococcus aureus* | Stipkovits | − | − |
| *Bordetela bronchiseptic* | Stipkovits | − | − |
| *Ersipelothrix rhusiophiae* | Stipkovits | − | − |
| *Haemophilus parasuis* | Stipkovits | − | − |
| *Corynebacterium* | Stipkovits | − | − |

TABLE 1-continued

STRAINS AND PCR RESULTS

| Strain | Source | MHP1/2 | MHP3/4 |
|---|---|---|---|
| pyogenes | | | |
| Pasteurella multocida | Stipkovits | – | – |
| Mycobacterium bovis | Stipkovits | – | – |
| Chlamydia trachomatis | Stipkovits | – | – |

REFERENCES

1. Whittlestone, P. (1979). Porcine mycoplasmas. In *The Mycoplasmas. Volume II. Human and Animal Mycoplasmas.* (Tully, J. G. & Whitcomb, R. F., eds) pp. 133–176. New York: Academic Press.
2. Barile, M. F. (1985). Current status on control of mycoplasmal diseases of man, animals, plants and insects. *Bulletin De L'Institut Pasteur* 83, 339–373.
3. Ro, L. H. & Ross, R. F. (1983). Comparison of *Mycoplasma hyopneumoniae* strains by serological methods. *American Journal of Veterinary Research* 44, 2087–2094.
4. Bolske, G., Strandberg, M., Bergstrom, K. & Johansson, K. (1987). Species-specific antigens of *Mycoplasma hyopneumoniae* and cross-reactions with other porcine mycoplasmas. *Current Microbiology* 15, 233–239.
5. Stemke, G. W. (1989). A gene probe to detect *Mycoplasma hyopneumoniae*, the etiological agent of enzootic pneumonia. *Molecular and Cellular Probes* 3, 255–232.
6. Johansson, K. E. (1992). Specificity of oligonucleotide probes complementary to evolutionarily variable regions of 16S rRNA from *Mycoplasma hyopneumoniae* and *Mycoplasma hyorhinis*. *Research in Veterinary Science* 52, 195–204.
7. Bej, A. K., Mahbubani, M. H. & Atlas, R. M. (1991). Amplification of nucleic acids by polymerase chain reaction (PCR) and other methods and their applications. *Critical Reviews in Biochemistry and Molecular Biology* 26, 301–334.
8. Harasawa, R. (1991). Detection of *Mycoplasma hyopneumoniae* DNA by the polymerase chain reaction. *Molecular and Cellular Probes* 5, 103–9.
9. Blanchard, A., Gautier, M. & Mayau, V. (1991). Detection and identification of mycoplasmas by amplification of rDNA. *FEMS Microbiology Letters* 81, 37–42.
10. Freundt, E. A. (1983). Culture media for classic mycoplasmas. In *Methods in Mycoplasmology. Volume 1. Mycoplasma characterization.* (Razin, S. & Tully, J. G., eds) pp. 127–135. New York: Academic Press.
11. Gardella, R. S., DelGiudice, R. A. & Tully, J. G. (1983). Immunofluorescence. In *Methods in Mycoplasmology. Mycoplasma characterization.* (Razin, S. & Tully, J. G., eds) pp. 431–439. New York: Academic Press.
12. Taylor-Robinson, D. (1983). Metabolic inhibition tests. In *Methods in Mycoplasmology. Mucoplasma Characterization.* (Razin, S. & Tully, J. G., eds) pp. 411–417. New York: Academic Press.
13. Laemmli, U. K. (1970). Cleavage of structural proteins during the assembly of the head of bacteriophage T4. *Nature* 227, 680–685.
14. Marmure (1961). A procedure for Isolation of DNA from microorganisms. *J. Mol. Bio.* 3, 109–118.
15. Maniatis, T., Fritsch, E. F. & Sambrook, J. (1982). *Molecular cloning: A laboratory manual.* Cold Spring Harbor, N.Y.: Cold Spring Harbor Laboratory.
16. Mandel and Higa (1970). Calcium Dependent Bacteriophaqe DNA Infection. *J. Mol. Bio.* 53, 154.
17. Southern, E. M. 1975. Detection of Specific Sequences Among DNA Fragments Separated by Gel Electrophoresis. *J. Mol. Bio.* 98, 503.
18. Rigby, Digman, Rhoades & Barg. 1977. Labeling DNA to High Specific Activity in Vitro by Nick Translation with DNA Polymerase I, *J. Mol. Bio.* 113, 237.
19. Sanger, F., Nicklen, S. & Coulson, A. R. (1977). DNA sequencing with chain terminating inhibitor. *Proceedings of the National Academy of Sciences USA* 74, 5463–5467.
20. Henikoff, S. (1984). Unidirectional digestion with Exonuclease III creates targeted breakpoints for DNA sequencing. *Gene* 28, 351–359.
21. Bereiter, M., Young, T. F., Joo, H. S. & Ross, R. F. (1990). Evaluation of the ELISA, and comparison to the complement fixation test and radial immunodiffusion enzyme assay for detection of antibodies against *Mycoplasma hyopneumoniae* in swine serum. *Veterinary Microbiology* 25, 177–192.
22. Jensen, J. S., Uldum, S. A., Sondergardandersen, J., Vuust, J. & Lind, K. (1991). Polymerase chain reaction for detection of *Mycoplasma genitalium* in clinical samples. *Journal of Clinical Microbiology* 29, 46–50.
23. Landgraf, A., Reckmann, B. & Pingoud, A. (1991). Direct analysis of polymerase chain reaction products using enzyme-linked immunosorbent assay techniques. *Analytical Biochemistry* 198, 86–91.

We claim:

1. An oligonucleotide primer pair for use in a PCR-based assay for *Mycoplasma hyopneumoniae*, wherein said pair comprises the nucleotide sequence 5'-AAGTTCATTCGCGCTAGCCC-3' (SEQ ID NO:1) and the nucleotide sequence 5'-GCTCCTACTCCATATTGCCC-3' (SEQ ID NO:2) and wherein said pair hybridizes to *Mycoplasma hyopneumoniae* but does not hybridize to *Mycoplasma hyorhinis*, *Mycoplasma flocculare* and *Mycoplasma hyosynoviae*.

2. A kit for use in detecting the presence of *Mycoplasma hyopneumoniae* DNA in a sample suspected of containing said DNA comprising:
 (a) a container; and
 (b) the primer pair of claim 1, in said container.

3. The kit of claim 2 further comprising a probe comprising the nucleotide sequence 5'-GGTAGCCCTTCCTTTGAGGT-3' (SEQ ID NO: 3) that hybridizes to an amplified target nucleic acid sequence resulting from the use of said primer pair in a polymerase chain reaction.

4. The kit of claim 3 further comprising means for detecting the hybridization of said probe to said amplified target nucleic acid sequence.

5. The kit of claim 3 wherein said probe is an oligonucleotide consisting of the nucleotide sequence 5'-GGTAGCCCTTCCTTTGAGGT-3' (SEQ ID NO: 3).

6. A method for detecting the presence of Mycoplasma hyopneumoniae in a first sample comprising the steps of:
 (a) isolating the DNA from said *Mycoplasma hyopneumoniae* in said first sample to form a second sample containing said isolated DNA;
 (b) amplifying a target nucleic acid sequence in said isolated DNA by a polymerase chain which results in an amplified target nucleic acid sequence wherein an oligonucleotide primer pair used in said reaction comprises the nucleotide sequence 5'AAGTTCATTCGCGCTAGCCC-3' (SEQ ID NO: 1) and the nucleotide sequence 5' GCTCCTACTCCATATTGCCC-3' (SEQ ID NO: 2) and wherein said pair hybridizes to *Mycoplasma hyopneumoniae* but does not hybridize to *Mycoplasma hyorhinis*, *Mycoplasma flocculare* and *Mycoplasma hyosynoviae*; and
 (c) detecting the presence of said amplified target nucleic acid sequence in said second sample as a means of detecting the presence of *Mycoplasma hyopneumoniae* in said first sample.

7. The method of claim 6 wherein said target nucleic acid sequence comprises nucleotides 810 to 1264 of the sequence shown in FIG. 4.

8. The method of claim 7 wherein said step of isolating said DNA comprises disrupting said *Mycoplasma hyopneumoniae* and extracting the DNA.

9. The method of claim 7 wherein said step of amplifying said target nucleic acid sequence comprises the steps of:
 (a) heating said second sample in the presence of four different nucleoside triphosphates and said oligonucleotide primer pair for an effective time and at an effective temperature to denature the DNA in said second sample, wherein each oligonucleotide primer is sufficiently complementary to different strands of said target nucleic acid sequence to hybridize therewith, such that the extension product synthesized from one oligonucleotide primer, when separated from its complement, can serve as a template for synthesis of the extension product of the other oligonucleotide primer;
 (b) cooling the denatured DNA to a temperature that promotes hybridization of each oligonucleotide primer to its complementary strand;
 (c) contacting the natured DNA, at the same time as or after step (a) or (b), with a thermostable enzyme that catalyzes the combination of the nucleoside triphosphates to form primer extension products complementary to each strand of DNA;
 (d) maintaining the mixture from step (c) at an effective temperature for an effective time to promote the activity of the enzyme and to synthesize, for the target nucleic acid sequence being detected, an extension product of each oligonucleotide primer that is complementary to each strand of the sequence, but not so high as to separate each extension product from its complementary strand;
 (e) heating the mixture from step (d) for an effective time and at an effective temperature to separate the primer extension products from the strands on which they were synthesized to produce single-stranded molecules, but not so high as to denature the enzyme irreversibly;
 (f) cooling the mixture from step (e) for an effective time and to an effective temperature to promote hybridization of each oligonucleotide primer to its complementary single-stranded molecule produced from step (e); and
 (g) maintaining the mixture from step (f) at an effective temperature for an effective time to promote the activity of the enzyme and to synthesize, for the target nucleic acid sequence being detected, an extension product of each oligonucleotide primer that is complementary to each strand, but not so high as to separate each extension product from its complementary strand, resulting in amplification of said target nucleic acid sequence if present, wherein steps (f) and (g) are carried out simultaneously or sequentially.

10. The method of claim 9 wherein steps (e), (f), and (g) are repeated at least 29 times.

11. The method of claim 10 wherein said thermostable enzyme is a polymerase from *Thermus aquaticus*.

12. The method of claim 11 wherein the temperature in steps (b) and (f) is from 54° C. to 58° C.

13. The method of claim 7 wherein said step of detecting the presence of said amplified target nucleic acid sequence comprises the steps of:
 (a) contacting the amplified target nucleic acid sequence with a probe comprising the nucleotide sequence 5'-GGTAGCCCTTCCTTTGAGGT-3' (SEQ ID NO: 3) which hybridizes to said target nucleic acid sequence; and
 (b) determining if hybridization has occurred.

14. The method of claim 7 wherein said step of detecting the presence of said amplified target nucleic acid sequence comprises the steps of:
 electrophoresing the amplified target nucleic acid sequence in a gel; and
 visualizing the amplified target nucleic acid sequence.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single (D) TOPOLOGY: linear (ii) MOLECULE TYPE: DNA (genomic)

(xi) SEQUENCE DESCRIPTION: SEQ ID NO:1:

AAGTTCATTC GCGCTAGCCC                                                                 20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GCTCCTACTC CATATTGCCC                                                                 20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGTAGCCCTT CCTTTGAGGT                                                                 20

(2) INFORMATION FOR SEQ ID NO:4:

(i) SEQUENCE CHARACTERISTICS:
        (A) LENGTH: 2334 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GGAATTCCAG CCAATCTTTT AATTAAAATT TTATCTTTAT ATTTGAAAAC TACCACATCA        60
TTTCGCTGAG GTTTTTTGAC ATTGTTAATA AAAATTTGTT GGCCATTTTT TAAGGTTGGA       120
AACATTGAGT TTCCTTCGAC ATTTATTAAT TGGTAGACAA AGATAAAAAG CGCAGAAACT       180
ATTAAAACAC AAGTAAAAAT AAAAATAACA CCAATAATTA AGCGATTTTT CTTAATAAAT       240
TTTAGAAATT TGTTACTTAA GTTTTAGAT TTTAACATAG TTATTAAATC TATTTCTTTG        300
ATATTTATC ATAAAAAAAC AATTTTAATT TTGATTTTA TAATAAAAAG TGCTGAATTT         360
GAGGCAAACA TACTAATTAA TATAAAATTC TATAGTAAAA TAATTTGATT TAGTAAAGAA       420
GTGACCTTTT ATTCTGATAT TTGCAAATAA TTCAATATTA TTCAATGTTT TATAAATATT       480
CTTCTTTCCT TATTTTTACT TTTTTTTTTT TTTTTTTTT TTTGTTAAAA TTATTGCATA        540
GTAAAATTTA AGTTAAAACC CAACAAACCT AACTTATAAA ACCGAAAGGA ATTAGTAATA       600
ATGCAAAATC TAAAAAGAA TCTAAAAAAA ATATCCTTAT TTTTCGGAAT TTTTGGTTCT        660
TTATGTACAA TTCTTACAAC AACCACAACA ACAATTTCTA TTAGAAATGA AAATGCAAAC       720
GGGTTTTATT CGGGGACAGA AAATATTAAA AATGCAAGTT CAATAGCTTC TACAATTTTT       780
TCCTCTGCTC TGGACCCATT TAAATCGTTA AGTTCATTCG CGCTAGCCCA AAAATATGTA       840
GATGATAAAT ATTTAAAAAT TGAACAAGAT AATTACGCAG GGAAATCTC GCTTCTCGGA        900
```

-continued

```
GCAAAATCCA TAGTTTATTT TGGTGGATTA TTTTGGGAAG ATAAAGTTGC ATGAGCAAGT    960
AATTTAACAG TAAAACATCA AAAAAAAGTA AGTCCATATT ATATAACAAG TAAGCCAAAA   1020
TATATTGAAG CAACCTTAAA AACTTGAACC TCGGGCTTAG GTAGCCCTTC CTTGAGGTA    1080
GGCGGGGAAA TAAAATATAA TGGTAATTTC AGATCTAATT TAGGTATAAA AATTGGAATA   1140
GATTATGGAA CTAGAGAATT ATTTATTACT AAAAGTGTTC AAAACCTACC ACAAGCTAAA   1200
ATAACTTATG CGGGTACGGG TTGGAGATAC AAAGTAACTT CATATGGGCA ATATGGAGTA   1260
GGAGCAATAG AAACTGAAGA TGAATTTTA ATGTTTAATA CTGAAAATTC AATGATTACA    1320
ACACGACGAA AAAGAAAACC TAAAACATCA TTTCCTGATA TTTAGGTCG TTATATCGAA     1380
GAAAAATACG GGCATTTACC TGAAGAAGAT GATAATAATT AATAACTTAA GTAAAAAGTT   1440
TGAAACTAAA TCGATTTTTG AAAAAATTAA TTTAGAAATT CCCACAAACA AACTAACTTT   1500
TGTAGTTGGC GAATCTGGGA TGGGAAAATC AACCTTAATT AATTTAATTG CCGGTTTTAC   1560
TAAAAAAGAT GAAGGTGAAA TTATCTTTTT TAAAGATGGA AAAGAAGAAA AAAATCCTTT   1620
AATTGATGTA GTTTTTCAGG ATTTTAACCT AATTGAAAAT CTTTCTGTTA AAAATAATAT   1680
TTTAATTGGA AATAGCTTAA TTCAAAAAGA ATTTGATCAA AATTTGCTTG AAAAAGAGC    1740
AAATTTTCTT AATATTGAAA ATGAAAAACT AAATCAACAA GTCAAAGATT TATCGGGTGG   1800
CGAGAAACAA AGAGTCGGTA TTTTACGTGC TTTTTCGCGA AATTCAGATT TTATTTTACT   1860
CGATGAACCA ACCGGAAATC TTGATGAGGA AAATGCAGTT GCTGTTTTG AAAATTTAAA    1920
AAAATTATCA AAAAACAAAA CTATTTGGT TGTTAGTCAC AATTTAGAAC TAGCAAAAAA    1980
ATATGCAGAT CAAATTATCC ATATCAAAAA AGATACTATT GATGTTGAAA CTTTTGACAA   2040
AAAGAAAAAA ACACAAGAAA ATGAGAGTGA AAATTCTGCT TTTGTTCAT AAATTGAACA    2100
AAAACCAGTT TTTAATTTTT TAACGAAATA TAAAACTGGT TTTTGCTAG CTTTTGCCGA    2160
TTTTAAAACA AAAATAACAA CTTTTATTTT ATTAATTATT GTTTTTTTG TTTTATAAG    2220
TGGGGGCACA TTGTTCACTT CACTACAGAT TTCTGCAAAA AATCTCAATT TGTCTAAGGT   2280
CCAGGAATAT AGTATGGACT CAGTAATTAT AAATAGACCA TTTATAGGAA TTCC         2334
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
TGTGTAGTTG GCCAATCTGG                                                 20
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
GATTTCCGGT TGGTTCATCG                                                 20
```